US 7,111,780 B2

(12) United States Patent
Broussard et al.

(10) Patent No.: US 7,111,780 B2
(45) Date of Patent: Sep. 26, 2006

(54) AUTOMATED DRUG SUBSTITUTION, VERIFICATION, AND REPORTING SYSTEM

(75) Inventors: Brian Broussard, Lafayette, LA (US); Samuel L. Nebiolo, Pittsburgh, PA (US); Jeffery Henry, Port Barre, LA (US)

(73) Assignee: McKesson Automation Systems Inc., Pittsburgh, PA (US)

( * ) Notice: Subject to any disclaimer, the term of this patent is extended or adjusted under 35 U.S.C. 154(b) by 0 days.

(21) Appl. No.: 10/688,505

(22) Filed: Oct. 17, 2003

(65) Prior Publication Data

US 2004/0138921 A1  Jul. 15, 2004

Related U.S. Application Data

(60) Provisional application No. 60/419,620, filed on Oct. 18, 2002.

(51) Int. Cl.
G06F 7/08 (2006.01)

(52) U.S. Cl. ........................................ 235/381; 235/380

(58) Field of Classification Search .............................. 235/462.01–462.25, 382, 375, 381, 380, 235/383, 432, 436
See application file for complete search history.

(56) References Cited

U.S. PATENT DOCUMENTS

| | | | |
|---|---|---|---|
| 4,171,065 A | 10/1979 | Hurst | |
| 4,918,604 A | 4/1990 | Baum | |
| 5,597,995 A | 1/1997 | Williams et al. | |
| 5,720,154 A | 2/1998 | Lasher et al. | |
| 5,762,235 A | 6/1998 | Coughlin | |
| 5,797,515 A | 8/1998 | Liff et al. | |
| 5,845,264 A | 12/1998 | Nellhaus | |
| 5,883,370 A | 3/1999 | Walker et al. | |
| 5,907,493 A | 5/1999 | Boyer et al. | |
| 6,098,892 A | 8/2000 | Peoples, Jr. | |
| 6,112,502 A | 9/2000 | Frederick et al. | |
| 6,155,485 A | 12/2000 | Coughlin et al. | |
| 6,181,982 B1 | 1/2001 | Yuyama et al. | |
| 6,202,923 B1 | 3/2001 | Boyer et al. | |
| 6,260,761 B1 | 7/2001 | Peoples, Jr. | |
| 6,318,630 B1 | 11/2001 | Coughlin et al. | |
| 6,385,505 B1 | 5/2002 | Lipps | |
| 6,393,339 B1 | 5/2002 | Yeadon | |

(Continued)

FOREIGN PATENT DOCUMENTS

EP        1 172 753        1/2002

(Continued)

OTHER PUBLICATIONS

US RE37,586, 03/2002, Williams et al. (withdrawn)

Primary Examiner—Thien M. Le
(74) Attorney, Agent, or Firm—Alston & Bird LLP (57) ABSTRACT

An integrated pharmacy system receives prescription information, creates a substitution reference list identifying the requested medical item and a plurality of equivalent medical items, automatically selects one of the items identified on the substitution reference list, fills the prescription, checks the accuracy of the filled prescription, facilitates the sales exchange, and creates an archive of the transaction, although not all steps need to be performed for every application. The integrated pharmacy system can also prevent unauthorized users from performing improper functions such as, for example, attempting to dispense an item which is not a proper substitute for the requested item. The present invention, by automatically substituting equivalent medical items for a requested medical item and by automatically archiving each prescription transaction, simplifies the prescription filling and record keeping requirements for the pharmacy technician and pharmacist.

43 Claims, 6 Drawing Sheets

U.S. PATENT DOCUMENTS

| | | | |
|---|---|---|---|
| 2002/0032582 A1 | 3/2002 | Feeney, Jr. et al. | |
| 2002/0095314 A1 | 7/2002 | Bodsworth et al. | |
| 2003/0189732 A1* | 10/2003 | Bean et al. | 358/302 |
| 2004/0172281 A1* | 9/2004 | Stanners | 705/2 |
| 2004/0215369 A1* | 10/2004 | Rosenblum | |
| 2005/0065645 A1* | 3/2005 | Liff et al. | 700/241 |
| 2005/0114122 A1* | 5/2005 | Uhrbach et al. | 704/220 |

FOREIGN PATENT DOCUMENTS

| | | |
|---|---|---|
| EP | 1 172 753 A2 | 1/2002 |
| EP | 1 172 753 A3 | 1/2002 |
| GB | 2368428 | 5/2002 |
| JP | 2002-092167 | 3/2002 |
| WO | WO 02/21402 | 3/2002 |

* cited by examiner

AUTOMATED DRUG SUBSTITUTION, VERIFICATION, AND REPORTING SYSTEM

CROSS-REFERENCE TO RELATED APPLICATIONS

The present application claims the benefit of U.S. Provisional Patent Application Ser. No 60/419,620 entitled "Automated Drug Number Substitution, Verification, and Reporting System" filed 18 Oct. 2002 and which is incorporated in its entirety herein by reference.

BACKGROUND OF THE INVENTION

The present invention relates generally to an integrated pharmacy system having hardware and software components that totally or partially automate the medical prescription fulfillment process from entry of the prescription to payment and, more particularly, a method for automatically generating dispensing information for a selected medical item.

Integrated pharmacy systems are used to streamline the prescription fulfillment process. An exemplary integrated pharmacy system is disclosed in U.S. Pat. No. 5,597,995 to Williams entitled "Automated Medical Prescription Fulfillment System Having Workstations For Imaging, Filling, And Checking The Dispensed Drug Product," issued 28 Jan. 1997 and incorporated by reference herein in its entirety.

The Williams patent discloses a pharmacy system for automating the medical prescription fulfillment process for a customer. It includes an imaging workstation having a host computer for receiving data entry of an original medical prescription for a prescribed drug product and customer information and for producing a prescription transaction data record, and an electronic communication device for communicating the prescription transaction data record from the host computer to a series of computers. A filling workstation includes dispensing apparatus for counting, dispensing, and packaging of the dispensed drug product into the drug vial for the customer. A checking workstation includes a scanner for scanning the bar code label on the drug vial, and a display for displaying the digitized image of the original medical prescription, and for displaying a digitized image of the prescribed drug product to allow a first visual comparison between the digitized image of the prescribed drug product and the dispensed drug product in the drug vial, and a second visual comparison between the digitized image of the original medical prescription and the dispensed drug product in the drug vial before it is given to the customer.

A common drug identifier used by integrated pharmacy systems is a National Drug Code (NDC). An NDC number is issued for each drug in the United States. The NDC is a 10-digit number typically containing three (3) segments or fields: the manufacturer or distributor code field, the product code field, and the package code field. The manufacturer or distributor code is assigned by the Food and Drug Administration (FDA), whereas the product and package codes are assigned by manufacturers or distributors.

The manufacturer or distributor code identifies the entity that manufactured or distributed the drug. The product code represents the drug name and strength. The package code represents the quantity (count, weight, mass or volume) in the stock container as delivered from the manufacturer or distributor. The three field representation may result in numerous NDC numbers being assigned to the same drug. Although numerous NDC numbers assigned to the same drug may be inefficient for drug identification, the NDC numbering scheme facilitates inventory management processes.

The NDC number may be represented in one of three different formats typically denoted as 4-4-2, 5-3-2 and 5-4-1. The first of the three segments represents the manufacturer or distributor code and may be either 4 or 5 digits. When the manufacturer code is 4 digits, the product code field will be 4 digits and the package code field will be 2 digits (i.e., the 4-4-2 format). When the manufacturer code is 5 digits, the manufacturer/distributor has an option of assigning either a 3 or 4 digit product code field followed by a 2 or 1 digit package code field (i.e., the 5-3-2 and 5-4-1 formats, respectively).

The NDC number is typically encoded on the stock container as a bar code using a UPC-A bar code symbology with a data format reserved for NDC numbers as defined by the Uniform Code Counsel (UCC). However, there are exceptions to the use of the UPC-A bar code symbology caused by manufacturer preferences, the dispensing of non-prescription products (i.e., over the counter (OTC) drug products), and delivery of non-pharmaceutical products (i.e., syringes, bandages and other supplies).

In addition to the NDC system used in the United States, foreign countries may use different drug identifiers. For example, Canada uses a Drug Identification Number (DIN) to identify drugs. The DIN is intended to represent a specific drug regardless of the manufacturer or distributor, however, it has been noted that manufacturers have unique DINs assigned to equivalent drugs (same drug name, strength, and therapeutic equivalence).

A Canadian drug package identifier uniquely identifies the quantity or amount of product within the stock container. A typical Canadian stock container uses the UPC-A bar code symbology and data formatting standards as defined by the UCC, however, there is no correlation between the UPC data value, DIN number, and package identifier. Because the UPC data value conforms to the UCC standard, the first 5-digits of the 10-digit UPC data value represents the manufacturer or distributor (as assigned by the UCC). The last 5-digits of the 10-digit UPC data value are assigned by the manufacturer or distributor as a product identifier. The 5-digit product identifier value creates a unique bar code value for each Canadian manufacturer and distributor for every drug and stock container quantity.

In addition to the NDC and DIN identifiers, other identification systems may be assigned (for example, by a manufacturer, supplier, pharmacy, etc.) to identify a medical item. For example, a general product index number (GPI), a general product code (GPC), and/or an internal reference code (IEN) may be assigned to a medical item by a manufacturer.

During a prescription filling transaction, it is common for a substitute drug to be dispensed in place of the specific drug that was requested (i.e., prescribed) by a treating physician. Drug substitution increasingly challenges US pharmacies trying to meet the reporting requirements related to a prescription filling transaction. The reporting requirements are typically established by third-party payors (e.g., an insurance company, Medicare, Medicaid, etc.). Third-party payors increasingly require more specific information on the actual drug dispensed to fill a prescription. Where in the past it may have been sufficient to report the drug and drug number as written by the physician, today the third-party payors may require that the exact drug name, drug number (e.g., NDC, DIN, GPI, etc.), and drug package size as dispensed be reported. In the future, it is anticipated that the third-party payors will require additional information on the actual drug dispensed. This may include the manufacturer's lot number or batch number to identify production specifics and the drug's expiration date from the manufacturer, distributor, labeler, or re-packager.

With prior art integrated pharmacy systems, the host computer's selection of a substitute drug to fill a prescription creates several problems. In a typical dispensing transaction, information (for example, from a physician, provider, pharmacy, customer, etc.) that is entered into the integrated pharmacy system is transmitted to a third-party clearinghouse for adjudication before the integrated pharmacy system activates a dispensing device. Adjudication refers to processing information entered into the integrated pharmacy system to determine whether a drug is approved by a third-party payor (i.e., determining if an insurance carrier will pay for, or reimburse a customer for, a given drug under a given insurance plan).

A problem inherent to prior art integrated pharmacy systems is that a new prescription label is not printed when a substitute drug is dispensed (i.e., the information related to the requested drug, not the substitute drug, is printed on the label). Although the requested and substitute drugs (or products) may be equivalent, they may be manufactured or distributed by different companies. Likewise, each drug may be identified by a unique manufacturer or distributor drug number or stock container indicia. Thus, substitution requires reliance on the pharmacy technician to dispense the proper substitute drug using a label that corresponds to the requested drug, not the drug selected for substitution. Additionally, substitution creates inventory and reporting problems which complicate the pharmacy's auditing procedures.

The multiple identification numbers for substitute drugs within a single identification system (e.g., multiple NDC numbers for the same drug), the multiple identification systems (e.g., the NDC system, the DIN system, etc.), and the increased reporting specificity required by third-party payors create burdens on pharmacy technicians and pharmacists tasked with filling a prescription. Ideally during the prescription fulfillment process, the pharmacy technician and pharmacist are focused on filling each prescription with the correct drug (i.e., name and strength). In reality, however, the pharmacy technician and pharmacist are distracted from this role by the multiple identification numbers for substitute drugs and the requirements established by third-party payors.

Thus, there exists a need for an integrated pharmacy system having hardware and software components that automate the medical prescription fulfillment process from entry of the prescription to payment. More specifically, there exists a need for a method of automatically generating dispensing information that may be used to manually or automatically fill a prescription with a requested drug or an appropriate substitute drug.

SUMMARY

The present invention is directed to a method comprised of receiving prescription information, automatically applying substitution rules, and automatically outputting dispensing information based on the application of the substitution rules. A variation of the method includes generating a substitution reference list based on the prescription information. The substitution reference list identifies at least one of the requested medical item (which may be a drug) or an equivalent medical item (which may be an equivalent drug).

In embodiments where the substitution reference list is generated, the substitution rules are applied to items on the substitution reference list.

The method of the present invention also includes dispensing based on the dispensing information. The dispensing can be performed manually, in which case the dispensing information may be location information (e.g., lighting an indicator on a bin, providing a location where a manual dispense may be performed, etc.). The dispensing can also be performed by automated dispensing equipment, in which case the dispensing information may be signals for operating the automated dispensing equipment.

The substitution rules may be, as described more fully below, rules embodying knowledge about the dispensing system hardware configurations, product availability, expiration date, cost, profit potential, inventory management, and workflow efficiencies. Substitution rules may also embody pharmaceutical equivalencies as defined by the pharmacy or a regulatory agency.

The present invention provides automated drug equivalency substitution based on, for example, knowledge of the dispensing equipment and inventory conditions. Other factors such as rules established by the FDA, State Board of Pharmacy, pharmacy chain, pharmacist, physician, insurer, and customer or patient may also be taken into account. The present invention also facilitates automated drug substitution with verification during the normal prescription fulfillment process, automated verification using the manufacturer supplied product identifier or system supplied identifier(s) (e.g., bar codes), automated reporting of the dispensed drug number to the various institutions, and automated traceability during all phases of the drug substitution. The present invention also automatically directs the pharmacy staff to the correct stock location of the dispensed product and automatically prints the correct prescription label based on the medical item actually used during the filling operation. The present invention simplifies the prescription filling and record keeping requirements for the pharmacy technician and pharmacist. These and other benefits of the present invention will be readily apparent from the detailed description which follows.

BRIEF DESCRIPTION OF THE DRAWINGS

To enable the present invention to be easily understood and readily practiced, the present invention will now be described for purposes of illustration and not limitation, in connection with the following figures wherein.

DETAILED DESCRIPTION

Figure 1:
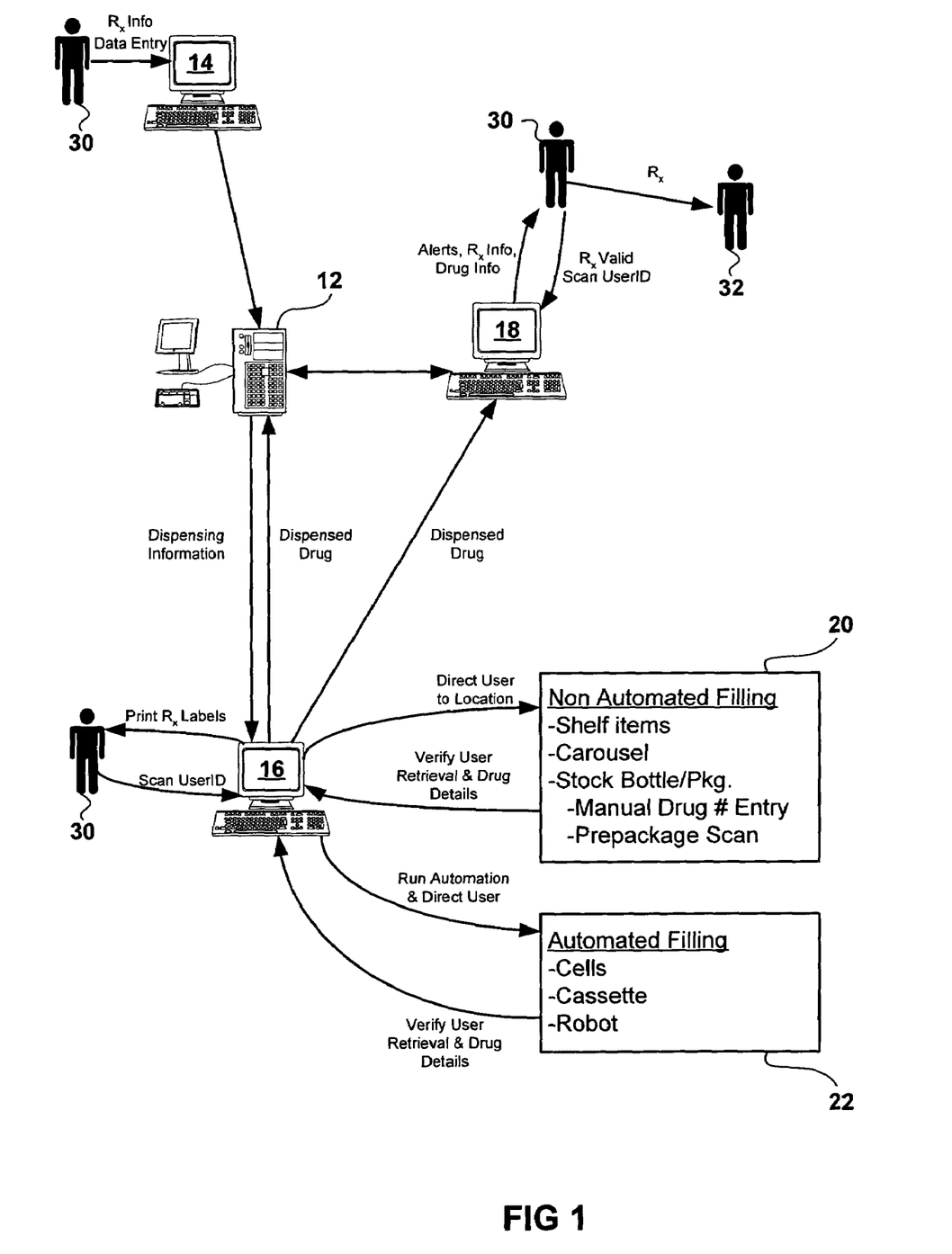
FIG. 1 is a simplified illustration of an integrated pharmacy system in which one embodiment of the present invention may be employed.

FIG. 1 is a simplified illustration of an integrated pharmacy system 10 incorporating one embodiment of the present invention. As shown in FIG. 1, the integrated pharmacy system 10 is comprised of a server 12, a data entry workstation 14, a fill workstation 16, and a check workstation 18, although other embodiments may be comprised of fewer or more components. In the current embodiment, the server 12, the data entry workstation 14, fill workstation 16, and check workstation 18 may each be comprised of a keyboard, a display, a processor (not shown), a communications device (not shown), and a data storage device (not shown). The processors are operable to accept various input data, execute sets of instructions which may be contained within the data storage devices, manipulate the various input data, and provide output results.

For simplicity of discussion, the integrated pharmacy system 10 is illustrated in FIG. 1 as being comprised of separate components. It should be apparent to those skilled in the art, however, that some of the components may be combined while remaining within the scope of the present invention. For example, the server 12, data entry workstation 14, fill workstation 16, and check workstation 18 may be combined in a single computer system operable to perform the functions of the individual components. Additionally, duplicate workstation components are also intended to be within the scope of the present invention. For example, multiple data entry 14, fill 16, and check workstations 18 may be used to simultaneously fill multiple prescriptions. The number and nature of the components comprising the integrated pharmacy system 10 is not important to understanding the present invention.

A workflow data depository for storing instructions and information received by, and/or generated by, the integrated pharmacy system 10 may reside on one or more of the data storage devices. In one embodiment, the workflow data depository resides on the server's 12 data storage device. The workflow data depository refers to a data structure that, in addition to containing the instructions and information as discussed above, may contain one or more databases having data fields used by the integrated pharmacy system 10 to complete the prescription fulfillment process, document transactions, inventory control, and the like. The data storage devices may also contain other data structures and/or databases while remaining within the scope of the current invention.

It should be apparent to one skilled in the art that the specific data fields, the number of datasets and their specific storage location within the integrated pharmacy system 10, the specific fields contained within each dataset, and the specific data structures used in the described embodiments are in no way intended to limit the scope of the present invention.

Accordingly, specific data fields, the number of datasets and their specific location, the specific fields contained within each dataset, and the specific data structures used may be altered while remaining within the scope of the present invention.

The communication devices (for example, a modem, network interface card, fax, etc.) may link the server 12 and workstations (14, 16, 18) to each other, to other components of the integrated pharmacy system 10, and to non-system devices (such as a third-party payor's system, a hospital's system, a third-party clearinghouse's system, and a physician's system, among others). Server 12, data entry workstation 14, fill workstation 16, and check workstation 18 may each also include an image scanner (not shown), a bar code scanner (not shown) for reading bar codes (such as on a container label), an RF tag reader (not shown), and a printer (not shown), as well as other peripheral components useful in such systems.

The data entry workstation 14 is used for receiving prescription information supplied by a customer 32, treating physician, etc. Prescription information refers to information needed to complete a dispensing transaction and may include information used to identify: the customer 32, the requested medication or treatment, possible adverse drug interactions and warnings, the prescribing physician, the pharmacy/person filling the prescription, and a third-party payor (e.g., insurance carrier), as well as other types of information that may be provided by either the prescribing physician, the pharmacy, or the customer 32. Prescription information may be manually entered into data-entry workstation 14 by a technician/pharmacist 30 using, for example, a keyboard or a scanner. Alternatively, prescription information may be automatically retrieved from a non-system computer (such as when a physician order entry is retrieved from a treating physician's computer) via a communication device. The prescription information may be stored within the workflow data repository, for example, on the data storage device of the data entry workstation 14 or on the data storage device within server 12, among others.

It should be noted that the term "drug", as used throughout this discussion, refers to any regulated or non-regulated pharmaceutical medication or over-the-counter medication regardless of its form (e.g., capsule, pill, ointment, etc.). It should be noted that the process described herein is also applicable to other articles and products (e.g., syringes, bandages, etc.) maintained or dispensed in a healthcare setting such that reference to "medical item" should be considered to include drugs as well as such other articles and products.

For the purposes of this document, "equivalent drug" refers to any drug that is granted equivalency by the pharmacy or a regulatory agency (e.g., the FDA). For example, equivalent drug may refer to two drugs with the same basic composition even though they have different equivalencies as defined by the FDA Orange Book. Likewise, "equivalent medical item" refers to any medical item that is granted equivalency by a pharmacy or regulatory agency (e.g., the FDA).

According to one embodiment, the prescription information is received by the integrated pharmacy system 10 and a medical item is identified to be dispensed. For example, prescription information may be entered into data entry workstation 14 by technician/pharmacist 30 or received by the integrated pharmacy system 10 from a third-party computer (e.g., the prescribing physician's computer). After receiving the prescription information and identifying the medical item, the server 12, for example, may apply one or more substitution rules to the prescription information to produce a substitution reference list. If an equivalent medical item is not permitted to be dispensed (e.g., the physician has issued a dispense as written order), the substitution reference list will identify only the requested (i.e., prescribed) medical item. If the substitution of an equivalent medical item is permitted, the substitution reference list may contain the requested medical item and one or more equivalent medical items that are within the integrated pharmacy system 10.

An adjudication may be then completed for one of the medical items on the substitution reference list. For example, a drug is selected from the substitution reference list and information identifying the selected drug (e.g., name, drug number, etc.) is transmitted to a third-party clearinghouse. An adjudication is completed and the results are transmitted back to the integrated pharmacy system 10. If the results of the adjudication are positive (i.e., the third-party clearinghouse determines that a third-party payor will pay for, or will reimburse a customer for, the selected medical item), the fill workstation 16 may output dispensing information for the selected medical item. If the results of the adjudication are negative (i.e., the third-party clearinghouse determines that a third-party payor will not pay for, or will not reimburse a customer for, the selected medical item), the integrated pharmacy system may notify the technician/pharmacist 30 and halt the fulfillment process.

In some instances, the third-party clearinghouse may return a positive result, but for a medical item that is different than the selected medical item. For example, the results for a generic drug may be returned in place of a brand name selected drug. In this instance, the technician/pharmacist 30 filling the prescription may be required to contact the prescribing physician before the generic drug can be dispensed. The fill workstation 16 facilitates the counting, dispensing, and packaging of medical item(s) for medical prescriptions either manually (see block 20) through a filling technician/pharmacist 30 or automatically (see block 22) via automated devices, or some combination thereof.

Typically, medical items are received in bulk in stock containers directly from the manufacturer and are dispensed into a customer container for a sales transaction. However, as used herein, stock container refers to any pharmacy defined container containing items that are repackaged into end user containers. Additionally, the term stock location may refer to any physical or virtual location used within a pharmacy to store or house stock containers or medical items. As used herein, end user containers may refer to vials, bottles, unit-of-use/unit dose containers (for example, blister packs), and/or any container in which the medical item is given to the customer. Some medical items may be received by the pharmacy pre-packaged, for example, in a unit-of-use/unit dose container. The integrated pharmacy system 10 is also capable of dispensing the correct quantity of a selected pre-packaged medical item.

With respect to non-automated filling 20, fill workstation 16 outputs dispensing information which typically informs the technician/pharmacist 30 of the location (e.g., the shelf, carousel, bin, etc.) within the pharmacy where the selected medical item can be found. The technician/pharmacist 30 manually retrieves the selected medical item, dispenses the correct amount, packages the dispensed medical item, and returns to the fill workstation 16.

For example, a carousel type system (not shown) may be used. The output dispensing information, in addition to providing location or other similar information, may include signals to cause the carousel to present the appropriate shelf selected by the fill workstation 16, and to illuminate a pick light to indicate the position on the shelf to find the medical item for the prescription being filled. Another non-automated dispensing location that may be used is a static shelf assembly (not shown) consisting of a plurality of non-movable shelves. In addition to identifying the shelf and bin by address, name, or other suitable information, signals may be generated to illuminate a pick-light corresponding to the selected medical item should this shelving be equipped with such lighting. If the selected item is, for example, a stock bottle of pills, the technician/pharmacist 30 counts out or determines the count by weighing the quantity of the selected drug.

Automated filling 22, on the other hand, does not require the technician/pharmacist 30 to find, dispense, and package the selected medical item. Automated filling 22 may be comprised of, for example, automated dispensing devices (not shown) electronically connected to fill workstation 16. Additionally, automated filling 22 may include a packaging station (not shown) which has an in-process holding component having a plurality of cubby holes with pick lights for each cubby hole. The holding component may be used for the in-process holding of a filled medical prescription before it is checked.

Automated filling 22 may include one or more different types of automated dispensing devices as are well known in the art. One type of automated dispensing device that may be used is a bank of instant access cells (not shown). Each instant access cell holds a drug and has an individual drop chute. Each cell has an identifier attached thereto. The cell has an internal counter which automatically counts out its contents in response to a dispensing request. The technician/pharmacist 30 places a vial at the mouth of the drop chute of the proper cell and releases the requested amount of drug into the vial to fill the medical prescription. The technician/pharmacist 30 then applies a cap to the filled vial.

Yet another automated dispensing device that may be used is a cassette-type system. A cassette-type system typically consists of a plurality of cassettes and a counting station. Each cassette has an identifier attached thereto. A robot moves one of the cassettes to the counting station where the correct amount of the drug is counted and dispensed into a labeled vial. The filled vial is then output. An example of this type of system is the AutoScript III available from McKesson Automation Systems Inc.

A combined non-automated/automated system is exemplified by a plurality of cassettes for use with a counting station, but where the technician/pharmacist 30 must manually label the vial, manually move the cassette to the counting station (and back), and manually move the vial.

Both non-automated filling 20 and automated filling 22 may provide feedback signals. Those of ordinary skill in the art will recognize that the feedback signals provided will depend upon the type of equipment and the workflow being implemented. For example, in a non-automated context, a validation device (such as a scale) may be used to generate a feedback signal indicative of the weight of the dispensed drug, which can be used as a check on the count. In an automated context, the feedback signal may include such information as the device filling the prescription, the identity of the technician/pharmacist 30, the status of the automated dispensing device, the lot number and the expiration date of the drug, etc.

The integrated pharmacy system 10 may provide a current reading of inventory for all medical items as they are used as well as provide an inventory update to inform the technician/pharmacist 30 when a particular medical item's replenishment is needed. As a result of the inventory-tracking ability, the integrated pharmacy system 10 warns the technician/pharmacist 30 of a low-inventory level and an out-of-stock situation of a particular medical item.

The automated dispensing devices mentioned above may also be used in combination with a packaging station (not shown). The function of the packaging station is to gather and package one customer's 32 or several customers' 32 (e.g., a family's) medical prescriptions in the integrated pharmacy system 10 prior to handing the order off for final checking at check workstation 18, or alternatively, after checking has already been completed.

The check workstation 18 may be used by a technician/pharmacist 30 to verify that the selected medical item and proper quantity for the selected medical item has actually been dispensed. The check workstation 18 may also be used to create updated records should an equivalent medical item be substituted and dispensed. The check workstation 18 stores the information related to the dispensed medical item in the work flow depository. By recording and reporting information related to the actual medical item dispensed, the pharmacy is insured of proper and timely reporting of the medical item dispensing transactions, even when a substitution occurs. The proper reporting may also include the quantity dispensed being different from the requested quantity, for example due to low inventory or out-of-stock limitations. The proper reporting eliminates the potential for future fines due to incorrectly reporting the actual medical item dispensing information to regulatory agencies. This also simplifies the auditing procedures performed by the pharmacy staff, for example, when a third-party audit occurs.

Knowledge of the medical item actually dispensed will assist the pharmacy during various post-dispensing tasks. These post-dispensing tasks include (but are not limited to) billing, auditing, and the identification of customers 32 to contact should a re-call occur for a particular medical item. In the context of a recall, the pharmacy staff can quickly identify which prescriptions were filled by the specific lot number and expiration date. In the context of an audit, the pharmacy staff can quickly respond as a result of having access to the specific dispensing records.

In the current embodiment, verification using the check workstation 18 occurs after an adjudication has been completed. For example, in the case where a technician/pharmacist 30 manually enters a medical item substitution at the fill workstation 14, the manually entered medical item substitution is adjudicated, dispensed, and then verified. In an alternative embodiment, verification using check workstation 18 may occur before the adjudication takes place. Again, in the case where a technician/pharmacist 30 manually enters a medical item substitution at the fill workstation 14, for example, the manually entered medical item substitution is dispensed, verified, and then adjudicated.

FIGS. 2A–2E are detailed illustrations of information contained on various labels used by the integrated pharmacy system of FIG. 1 according to an embodiment of the present invention. Referring to FIGS. 2A–2E, an original manufacturer stock container or package 40, a boxed product 50, customer container 60, dispensing device 70, and two tubes of medication 80a, 80b, respectively, are shown.

Figure 2A:
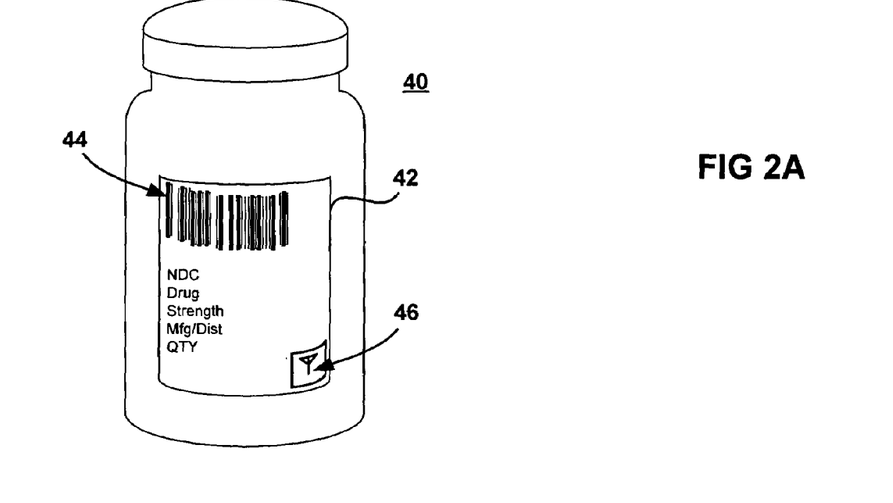
FIGS. 2A–2E are detailed illustrations of information contained on various labels used by the integrated pharmacy system of FIG. 1 according to one embodiment of the present invention.

The stock container 40 of FIG. 2A has a label 42 with a bar code 44 and/or RF identification tag 46 for proper identification of the stock container 40, its location, and/or its contents. The label 42 may also contain other identifying information (such as required by law) in human readable form, for example, drug name, drug number, drug strength, lot number, manufacturer/distributor name, quantity, etc.

Figure 2B:
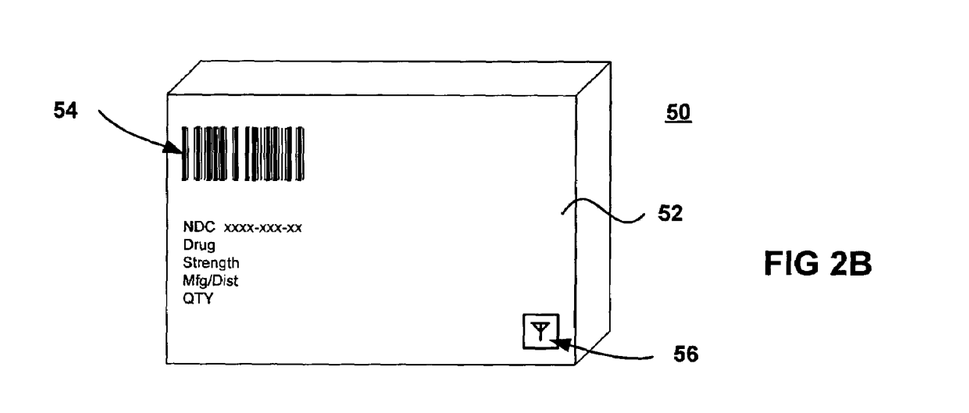

The boxed product 50 of FIG. 2B has a label 52 with a bar code 54 and/or RF identification tag 56 for proper identification of the boxed product 50, its location, and/or its contents. The label 52 may also contain other identifying information (such as required by law) in human readable form, for example, drug name, drug number, drug strength, lot number, manufacturer/distributor name, quantity, etc.

Figure 2C:
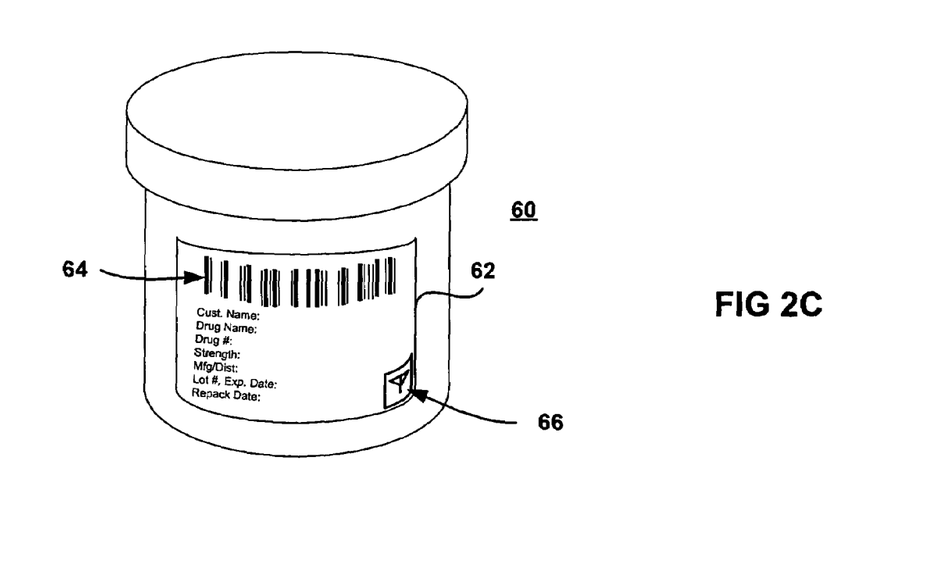

The customer container 60 of FIG. 2C has a label 62 with a bar code 64 and/or RF identification tag 66 for proper identification of the customer container 60 and/or its contents. The label 62 may also contain other identifying information (such as required by law) in human readable form, for example, customer name, physician name, drug name, dosage, drug number, drug strength, lot number, manufacturer/distributor name, expiration date, quantity, repack date, etc.

Figure 2D:
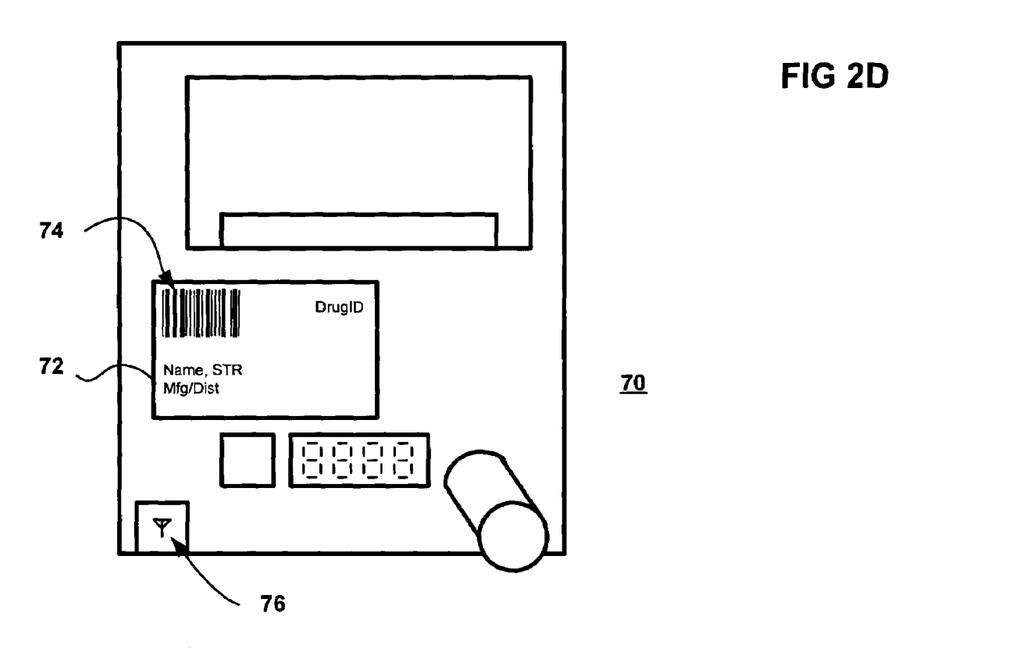

The dispensing device 70 has a label 72 with a bar code 74 and/or RF identification tag 76 for proper identification of the dispensing device 70. For example, the fill workstation 16 may instruct the technician/pharmacist 30 to obtain drugs from one of many dispensing devices 70. The correct dispensing device 70 can be found and verified by the technician/pharmacist 30 scanning the bar code 74 or scanning the RF identification tag 76. The label 72 may also contain other identifying information in human readable form, for example, drug name, drug number, drug strength, lot number, manufacturer/distributor name, etc.

Figure 2E:
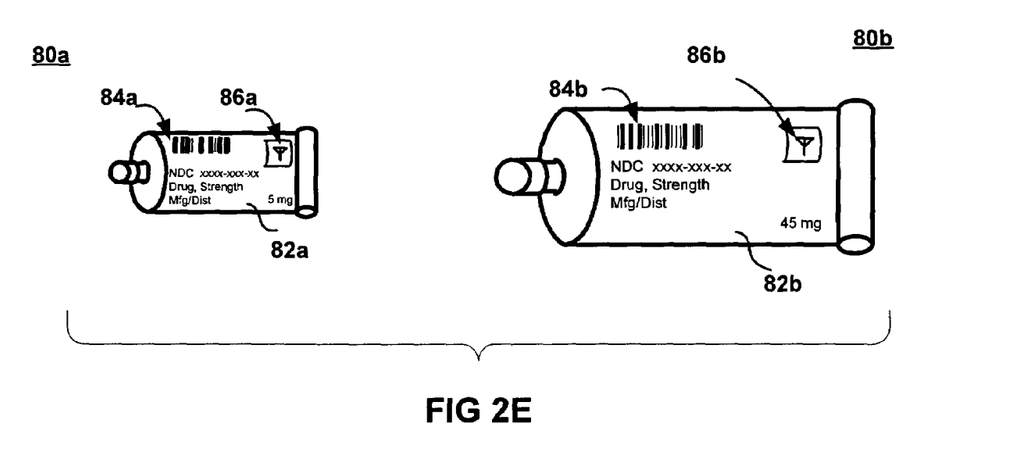

The medication tubes 80a, 80b each have a label 82a, 82b with a bar code 84a, 84b and/or RF identification tag 86a, 86b for proper identification of the medication tube 80a, 80b and/or its contents. The labels 82a, 82b may also contain other identifying information (such as required by law) in human readable form, for example, drug name, drug number, drug strength, lot number manufacturer/distributor name, quantity, etc. It should be noted that the bar codes 84a, 84b, the RF identification tab 86a, 86b, and printed information are slightly different for each tube. Specifically, the quantity value is different (as shown, 5 mg vs. 45 mg) so that the amount of medication prescribed can be accurately controlled.

Figure 3:
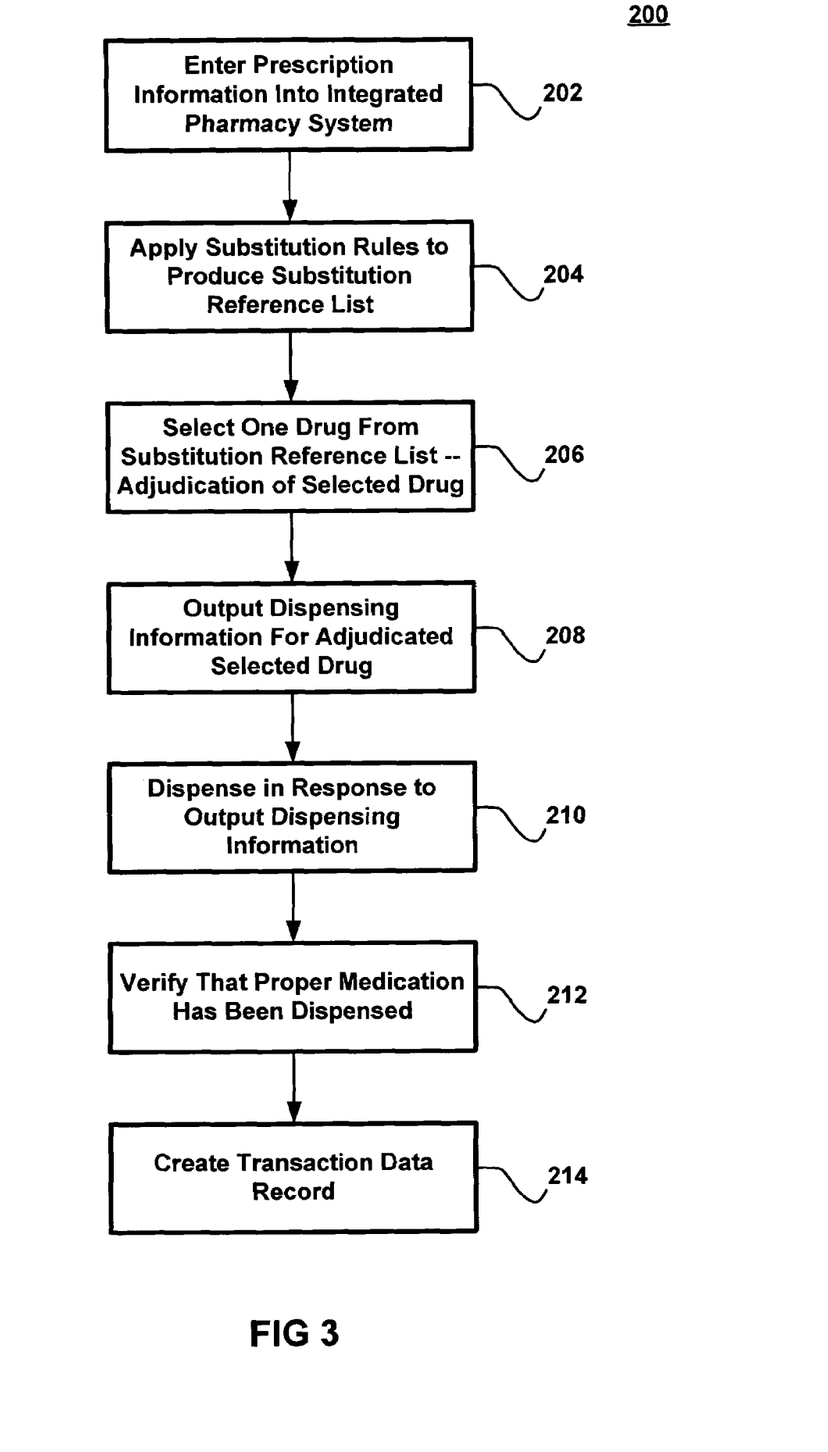
FIG. 3 is an operational process for filling a prescription using the integrated pharmacy system of FIG. 1 according to one embodiment of the present invention.

FIG. 3 illustrates operational process 200 for filling a prescription for a drug using the integrated pharmacy system of FIG. 1 according to one embodiment of the present invention. In the current embodiment, filling process 200 begins when prescription information is entered into the integrated pharmacy system 10 in operation 202. For example, a customer 32 presents the treating physician's handwritten prescription (i.e., a prescription for a requested drug) to the technician/pharmacist 30. The customer 32 may also verbally provide other information (such as required personal information) to the technician/pharmacist 30, who enters the information into the data entry workstation 14. The prescription information, in the current embodiment, is stored in a workflow data repository located within the server's 12 data storage device. It should be noted that although the discussion of operational process 200 in the current embodiment is directed only to filling a drug prescription, it should be apparent to one skilled in the art that operational process 200 may also be used to fill prescriptions for other medical items.

In the current embodiment, the data entry workstation 14 may also create a prescription order sheet. The prescription order sheet may include a bar code label containing a prescription number (i.e., $R_x$Num) or another number that is used by the pharmacy to track the progress of the prescription during the fulfillment process. The technician/pharmacist 30 may scan the bar code label from the prescription order sheet and may then use an image scanner to create a digital image of the treating physician's handwritten prescription. The digital image of the handwritten prescription may be stored within the server's 12 data storage device and may be linked to the prescription number (i.e., $R_x$Num) from the prescription order sheet. The original handwritten prescription may be filed away by the technician/pharmacist 30 as a permanent record for state and federal agencies.

After the prescription information is entered in operation 202, the prescription information as well as substitution rules (for example, medical item equivalencies as established by the pharmacy) may be used to create a substitution reference list in operation 204. In the current embodiment, the server 12 may apply one or more substitution rules to the prescription information to create the substitution reference list. The substitution reference list identifies the requested drug (i.e., the drug prescribed by the treating physician) and any equivalent drugs that may be dispensed in place of the requested drug. Each drug on the substitution reference list may be identified by name, quantity, strength, number, or other convenient manner. Third-party restrictions, a dispense as written order, etc., may cause the substitution reference list to contain only the requested drug (i.e., may prohibit an equivalent drug from being substituted).

After the substitution reference list is created in operation 204, the substitution rules are applied at 206 to select one of the drugs on the substitution reference list for dispensing. The substitution rules used to select one of the drugs may be based upon, for example, dispensing system hardware configurations, medical item availability, medical item expiration date, cost, pharmacy profit potential, inventory management, work flow efficiencies (e.g., medical items' location relative to a pharmacy worker's location), and customer 32 preferences (e.g., brand name over generic drugs). Rules established by the FDA, State Board of Pharmacy, technicians/pharmacists 30, physicians, insurers, and customers 32 may also be taken into account. Thus, specific information incorporating knowledge of the dispensing equipment and inventory, as well as other factors and conditions, may be encoded in the substitution rules. For example, the substitution rules may cause one of the drugs on the substitution reference list to be picked over the others based on such factors as expiration date and inventory count at each location.

After one of the drugs on the substitution reference list is selected, an adjudication may be performed. In the current embodiment, for example, information identifying the drug selected from the substitution reference list may be transmitted to a third-party clearinghouse. An adjudication may be completed for the selected drug by the third-party clearinghouse and the results of the adjudication may be transmitted back to the integrated pharmacy system 10. In the current embodiment, if the results of the adjudication are positive (i.e., the third-party clearinghouse determines that a third-party payor will pay for, or will reimburse a customer for, the selected medical item), the fill workstation 16 may output dispensing information for the selected medical item. If the results of the adjudication are negative (i.e., the third-party clearinghouse determines that a third-party payor will not pay for, or will not reimburse a customer for, the selected medical item), the integrated pharmacy system may notify the technician/pharmacist 30 and halt the fulfillment process.

In some instances, the third-party clearinghouse may return a positive result, but for a medical item that is different than the selected medical item. For example, the results for a generic drug may be returned in place of a brand name selected drug. In this instance, the technician/pharmacist 30 filling the prescription may be required to contact the prescribing physician before the generic drug can be dispensed. In an alternative embodiment, the integrated pharmacy system 10 is operable to complete the adjudication independent of the third-party clearinghouse.

After the adjudication results are returned to the integrated pharmacy system 10 in operation 206, the fill workstation 16 may then output dispensing information related to the selected drug (for example, if the adjudication results are positive) in operation 208. Dispensing information may take a variety of forms based on the pharmacy equipment and work flow. In the case of non-automated equipment, the dispensing information may include a simple identification of a location, or it may include an identification of a location together with the operation of pick lighting and/or the operation of locks in the case of locked cabinets. In the case of automated equipment, the dispensing information typically includes all information needed for the automated equipment to automatically dispense the drug. Operation 210 in FIG. 3 represents either a manual dispense or an automated dispense, or some combination thereof, which occurs in response to the dispensing information output by operation 208.

After a drug has been dispensed in operation 210, a verification may be completed in operation 212 to insure that the drug actually dispensed is the selected drug. In the current embodiment, a technician/pharmacist 30 may use the check workstation 18 to verify that the selected drug, in the proper quantity, has been dispensed.

In one embodiment, the technician/pharmacist 30 may initiate the checking process by downloading, scanning, or manually entering the information contained on the prescription order sheet. If an equivalent drug was substituted during the fulfillment process, the technician/pharmacist 30 may be notified by a visual and/or audible alert from the check workstation 18. If an error occurred during the drug substitution (for example, a technician/pharmacist 30 attempted to manually enter an improper substitute drug request), the technician/pharmacist 30 may be notified by another visual and/or audible alert from the check workstation 18. The visual alert may require the technician/pharmacist 30 to confirm the error for tracking purposes.

The check workstation 18 may also be used to check the medical prescription's refill status. If the current prescription transaction is a refill, the check workstation 18 may check the identity of the drug from the previous prescription filling transactions against the identity of the drug for the current transaction. If a difference is detected, the check workstation 18 may inform the technician/pharmacist 30 via a visual or audible alert. This alert allows the technician/pharmacist 30 to further counsel the customer 32 that the change occurred only because of manufacturer/distributor change in the product and that the medication dispensed is not a different medication. These changes might be apparent to a customer 32 as a result in a change in the size, shape, imprint, color, etc. to the drug itself. This allows the technician/pharmacist 30 to improve the level of customer service by proactively counseling the customer 32.

In the current embodiment, the check workstation 18 provides a high level of verification by displaying the digitized image of the original handwritten prescription from the treating physician (as entered at the data entry workstation 14) and a digitized image of the drug selected to be dispensed (i.e., either the requested drug or an equivalent drug). The original handwritten prescription and the image of the drug selected to be dispensed are compared with the actual drug dispensed (or an image thereof) being given to the customer 32. A zoom feature on the digitized images being viewed enables the technician/pharmacist 30 to see the necessary details to make an accurate and proper verification of the dispensed drug. The zoom feature on the handwritten prescription image may also be used to investigate possible alterations to the original handwritten prescription. A final quality control check requires that an authorized technician/pharmacist 30 verify that the prescription was filled properly by scanning his or her personal bar code.

Once the fulfillment process has been completed and checked in operation 212, a transaction data record is created and information related to the dispensing transaction is recorded in operation 214. The transaction data record in the current embodiment may consist of approximately 20 fields of information, which contain a variety of data input regarding the prescription and filling thereof needed for reporting and auditing purposes. For example, the transaction data record may include data fields for the prescription number, the NDC number, and the quantity of drug requested. The transaction data record may also include the drug number and/or related drug product specifics of the requested drug and of the drug actually dispensed (e.g., of an equivalent drug). The transaction data record may be communicated to the server 12 and stored in the workflow data repository. After operation 214 is completed, operational process 200 may be terminated.

Figure 3A:
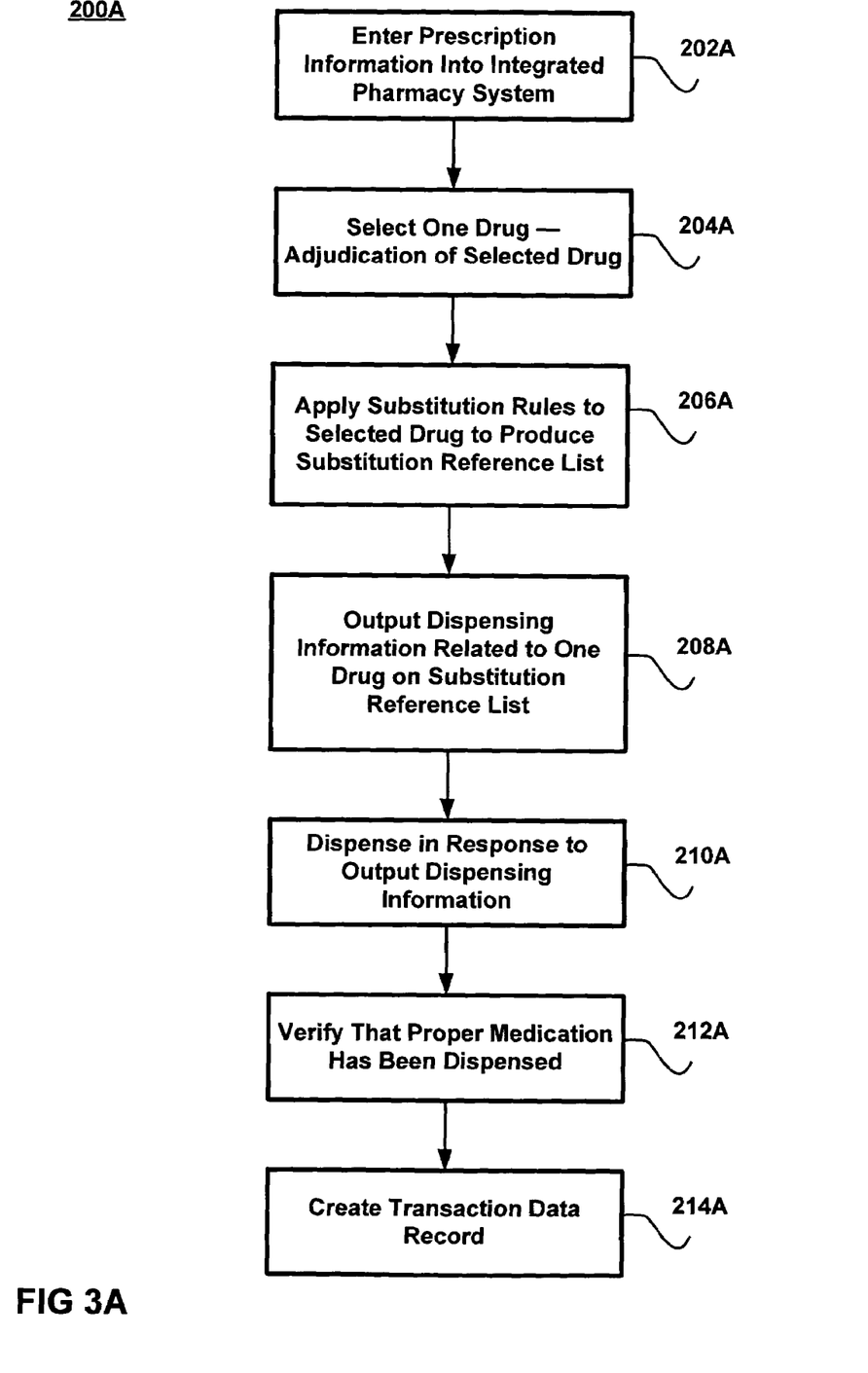
FIG. 3A is an operational process for filling a prescription using the integrated pharmacy system of FIG. 1 according to another embodiment of the present invention.

FIG. 3A is an operational process 200A for filling a prescription using the integrated pharmacy system of FIG. 1 according to another embodiment of the present invention. Operational process 200A has several operations in common with operation 200 as discussed above in conjunction with FIG. 3. For example, operation 202A may be the same as, or similar to, operation 202. Accordingly, in the current embodiment, filling process 200A begins when prescription information is entered into the integrated pharmacy system 10 in operation 202A. For example, a customer 32 presents the treating physician's handwritten prescription (i.e., a prescription for a requested drug) to the technician/pharmacist 30. The customer 32 may also verbally provide other information (such as required personal information) to the technician/pharmacist 30, who enters the information into the data entry workstation 14. The prescription information, in the current embodiment, is stored in a workflow data repository located within the server's 12 data storage device.

After the prescription information is entered in operation 202A, the requested (i.e., prescribed) drug is selected based upon the entered prescription information and an adjudication may be completed in operation 204A for the selected drug. In the current embodiment, for example, information identifying the selected drug may be transmitted to a third-party clearinghouse, an adjudication completed by the third-party clearinghouse, and the results of the adjudication transmitted back to the integrated pharmacy system 10. In an alternative embodiment, the integrated pharmacy system 10 is operable to complete the adjudication independent of the third-party clearinghouse. If the results of the adjudication are negative, the integrated pharmacy system 10 may notify the technician/pharmacist 30 and halt the fulfillment process. If the results of the adjudication are positive, the fulfillment process may continue.

After the adjudication results are transmitted back to the integrated pharmacy system 10 in operation 204A, the fill workstation 16 may apply one or more substitution rules to the selected drug to create the substitution reference list in operation 206A. The substitution reference list identifies the requested drug and any equivalent drugs that may be dispensed (according to the substitution rules) in place of the requested drug. Each drug on the substitution reference list may be identified by name, quantity, strength, number, or other convenient manner. Third-party restrictions, other restrictions, a dispense as written order, etc., may cause the substitution reference list to contain only the requested drug (i.e., may prohibit an equivalent drug from being substituted).

After the substitution reference list is created in operation 206A, the integrated pharmacy system 10 may select one drug from the substitution reference list using the substitution rules and may transmit information related to the selected drug to the third-party clearinghouse for a pre-dispense adjudication if the selected drug is not the same as the adjudicated drug from operation 204A. The third-party clearinghouse returns the result of the pre-dispense adjudication to the integrated pharmacy system 10. If the results are positive, the filling workstation 16 may output dispensing information related to the selected drug in operation 208A.

Alternatively, adjudication may be completed after a drug selected from the substitution reference list is dispensed (i.e., a post-dispense adjudication). In this instance, fill workstation 16 may output dispensing information related to the selected drug and the selected drug may be dispensed in operation 210A. The integrated pharmacy system 10 may transmit information related to the dispensed drug to the third-party clearinghouse for a post-dispense adjudication. The results of the post-dispense adjudication are then returned to the integrated pharmacy system 10. If the results of the post-dispense adjudication are negative, the integrated pharmacy system 10 may notify the technician/pharmacist 30 and the dispensed drug must be returned to stock. If the results of the adjudication are positive, the integrated pharmacy system 10 may notify the technician/pharmacist 30 and the transaction may be completed.

Alternatively, adjudication may be skipped altogether. In this instance, fill workstation 16 may output dispensing information related to the selected drug on the substitution reference list in operation 208A and the selected drug may be dispensed in operation 210A.

Operation 210A in FIG. 3A represents either a manual dispense or an automated dispense, or some combination thereof, which occurs in response to the dispensing information output by operation 208A. After a drug has been dispensed in operation 210A, a verification may be completed in operation 212A to insure that the drug actually dispensed is the drug selected from the substitution reference list. Once the fulfillment process has been completed and checked in operation 212A, a transaction data record is created and information related to the dispensing transaction is recorded in operation 214A. It should be noted that operations 202A, 210A, 212A, and 214A in operational process 200A may be the same as, or similar to, operations 202, 210, 212, and 214, respectively, in operational process 200.

Figure 4:
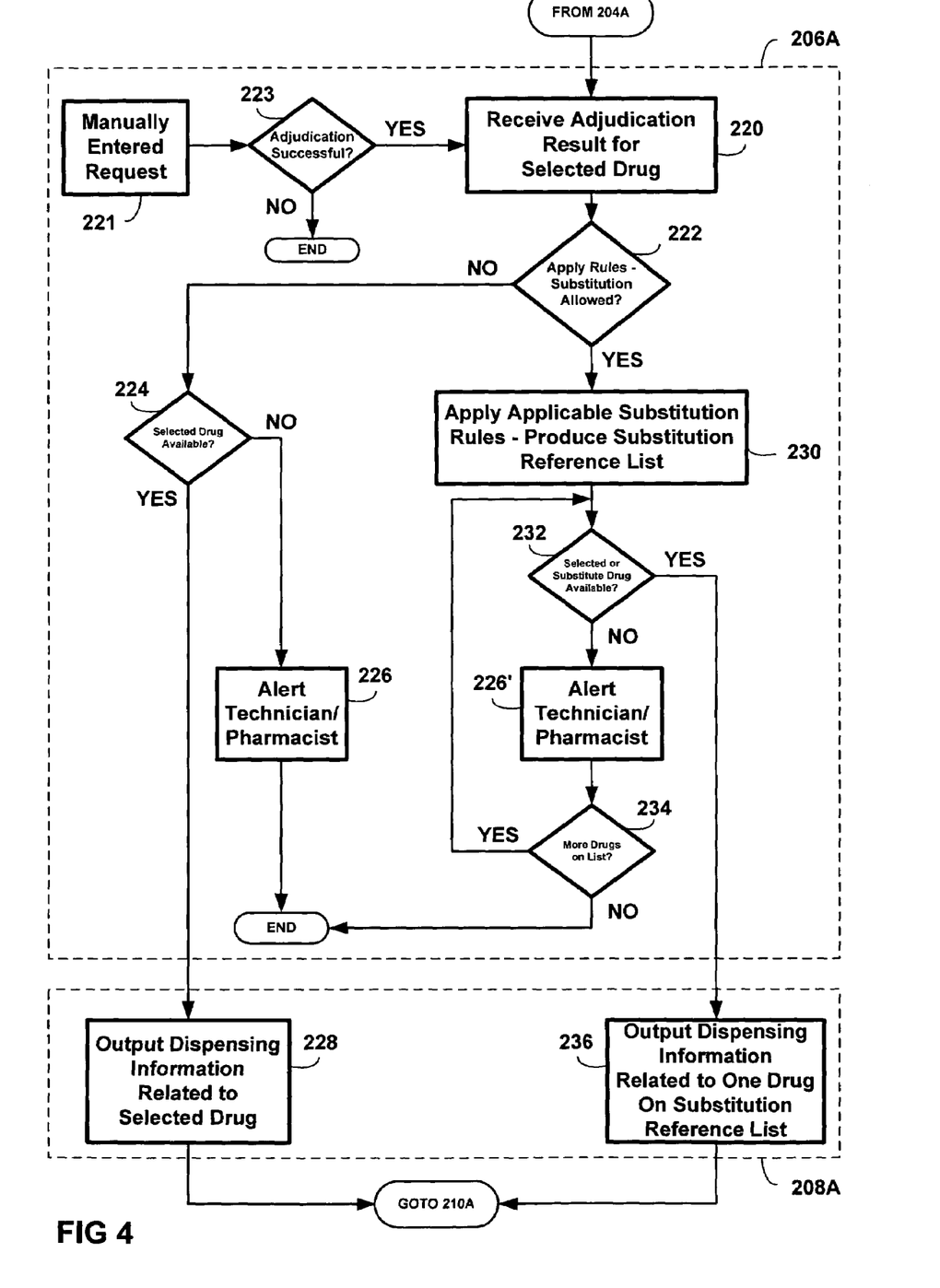
FIG. 4 is a more detailed illustration of some of the operations in FIG. 3A according to an embodiment of the present invention.

FIG. 4 is a more detailed illustration of operations 206A (i.e., apply substitution rules) and 208A (i.e., outputting dispensing information) of FIG. 3A according to an embodiment of the present invention. In operation 220, the adjudication result is received from operation 204A (as discussed above). Alternatively, the technician/pharmacist 30 may manually override the drug selected in operation 204A and manually enter (at operation 221) a selected drug to dispense.

When a request to dispense another drug is manually entered at 221, the integrated pharmacy system 10 communicates information identifying the manually entered drug to the third-party clearinghouse. The third-party clearinghouse adjudicates (at operation 223) whether the drug manually selected by the technician/pharmacist 30 may be dispensed in place of the requested drug. If the results of the adjudication are positive, process flow continues with operation 220. If the results of the adjudication are negative, the fulfillment process may be halted and an alert is issued.

During operation 221, the technician/pharmacist's 30 security level may be checked to insure that an override of the automatically selected drug is authorized. If an override is permitted, the technician's/pharmacist's 30 specific override frequency may be checked to confirm that they have not exceeded a pre-defined level. If the override is permissible, the prescription fulfillment process is allowed to continue, although the transaction is logged in the database for purposes of permitting review and creating an audit trail.

At operation 222, various substitution rules begin to be applied to the selected drug. It is anticipated that the substitution rules will likely be applied in some hierarchical manner. Rules that do not permit substitution, even though alternative medical items have been identified, may be applied first. For example, an insurance carrier may have a policy of not paying for certain drugs, even though they have been designated within the integrated pharmacy system 10 as equivalent. Thus, those rules would be applied first to determine if substitution is allowed.

If a prescription substitution is not allowed (for example because of a dispense as written restriction, a third-party restriction order, etc.), operational control branches NO and operation 224 assumes control. An availability check is completed in operation 224 and a determination is made as to whether the selected drug (i.e., from operation 204A or from operation 221) is available. It should be noted that the availability of a drug may depend on the drug's inventory level, the status of automated dispensing devices or non-automated dispensing locations where the drug is stored, and the user's access level, among others.

If the selected drug is not available, operational control branches NO and the technician/pharmacist 30 is alerted that the selected drug (i.e., from operation 204A) is unavailable in operation 226 and the process ends. If the selected drug is available, operational control branches YES and dispensing information related to the selected drug is output in operation 228. After the dispensing information is output, the process continues with operation 210A (as shown in FIG. 3A).

Returning to operation 222, if it is determined that a substitution is allowed, operational control branches YES and operation 230 assumes control. In operation 230, the fill workstation 16 applies certain of the applicable substitution rules to produce the substitution reference list. The substitution reference list may contain the selected drug (i.e., from operation 204A or from operation 223) and the equivalent drugs that are permitted to be dispensed as a substitute.

In producing the substitution reference list, operation 230 may also apply user security rules. For example, if a technician/pharmacist 30 does not have the required security level to dispense one or more of the drugs on the substitution reference list, the fulfillment process may be terminated.

After substitution reference list is created in operation 230, an availability check is completed in operation 232 and a determination is made as to whether one or more of the drugs on the substitute reference list are available. If one or more of the drugs are not available, operational control branches NO and the technician/pharmacist 30 is alerted that the selected drug (i.e., from operation 204A or from operation 221) or substitute drugs are unavailable in operation 226'. In one embodiment, if a first drug on the list is not available, the fill workstation 16 checks if there are more drugs on the substitution reference list at operation 234. If not, the process ends. If so, the process returns to operation 232 to determine the availability of another drug from the substitution reference list. The availability of the second drug is checked at step 232 and the process repeated until either a drug is found to be available or all items on the substitution reference list have been exhausted. If one of the drugs on the substitute reference list is available, operational control branches YES and control is transferred to operation 236. After the dispensing information is output in operation 236, the process continues with operation 210A (as shown in FIG. 3A). As discussed above, adjudication of a substitute drug may take place before or after the dispensing operation, or adjudication may be skipped completely.

In the current embodiment, the technician/pharmacist 30 is notified (visually or audibly) when information related to an equivalent drug has been output in operation 236. Notification helps the technician/pharmacist 30 realize that differences may exist between the selected drug (i.e., as prescribed by the physician) and equivalent drug dispensed.

The process flow in FIG. 4 is intended to illustrate what happens conceptually; it is not necessarily a representation of a particular implementation. For example, the substitution rules could be applied in such a manner that a "current best choice" is held in memory. As the substitution rules are applied, a new "current best choice" may replace the current "current best choice" in memory. Thus, at the end of application of all the applicable rules, the "current best choice" becomes the "selected drug." In such an implementation, the serial storing of one or more "current best choices" is the "list" with the "selecting" being the last stored "current best choice."

Some drug equivalencies may require additional action at the pharmacy prior to substitution. These changes are typically due to a drug being therapeutically equivalent to the requested drug, but with slight differences that would require a doctor's approval before substitution. The system would inform the filling technician/pharmacist 30 of such a requirement and prevent the filling from continuing without specific override notification. This override may take the form of a comment being entered based on the specifics in communicating with the doctor.

In certain embodiments, the technician/pharmacist 30 may be required to scan or enter his user ID before the fill workstation 16 will activate the automated dispensing equipment or inform the technician/pharmacist 30 of the location within the pharmacy where the selected medical item can be found. A user ID scan or user log-on may be required before dispensing begins to prevent an unauthorized technician/pharmacist 30 from dispensing a medication they do not have authority to handle (e.g., narcotics, controlled substances, special drugs, compounds, or other medications, as established law, by pharmacy rules, etc.) A user ID scan or user log-on requirement may also insure that a technician/pharmacist 30 has sufficient training to perform such special functions associated with drug substitutions and has other abilities needed to complete the prescription fulfillment process. A user ID scan or user log-on requirement may also allow for an audit trail to be generated. Once a user ID is scanned or entered into the system, the fill workstation 16 uses the information stored in its database to verify that the technician/pharmacist 30 is an authorized user.

The user ID scan or user log-on may limit the technician/pharmacist's 30 access to the system for completing each step needed to fill a specific prescription. Alternatively, the user ID scan or user log-on may allow the technician/pharmacist 30 to log onto a given workstation and be responsible for all operations initiated from that workstation, or to control multiple prescription filling functions from a single workstation location.

Once authorization is verified, the technician/pharmacist 30, for non-automated dispensing locations, is directed to a shelf location or standard shelving units containing the selected drug's stock container. The selected stock container is retrieved and its bar code indicia (or RF tag, etc.) is scanned using a bar code scanner (or RF tag reader, etc.). The stock container bar code indicia is compared to the database to determine the drug number, package size, and package size substitution rules. If the stock container's drug number matches the selected drug's drug number, the prescription filling is allowed to continue. If the stock container's drug number does not match, the package size substitution rules are first checked to see if the root drug numbers (i.e., the manufacturer/distributor code and the product code as previously discussed) match. If the root drug numbers match and the only difference is package size, the prescription filling is allowed to continue.

If the stock container's drug number does not match the selected drug's drug number, equivalencies for this stock container's drug number are found. If the stock container's drug number does not match the selected drug and the drug within the stock container is not equivalent to the selected drug, the transaction is logged in the workflow data depository for further review. The technician/pharmacist 30 is informed of the error in filling via visual and audible alerts. The prescription filling is not allowed to proceed if an error occurs. If the drug within the stock container is found to be equivalent to the selected drug, prescription filling is allowed to continue, and the drug image and other details are updated on the fill workstation 16 to the actual drug being dispensed for reference by the technician/pharmacist 30.

If automated dispensing equipment is used, the technician/pharmacist 30 will be provided with the filled prescription or directed to the location where the filled prescription can be retrieved. The technician's/pharmacist's 30 retrieval from the automated dispensing equipment can be monitored through signals produced by the automated dispensing equipment. Alternatively, the technician/pharmacist 30 may be required to scan the bar code indicia at the dispensing location before the selected drugs are dispensed into the vial from the location and scan the label containing the prescription number (e.g., from the prescription order sheet). The system 10 confirms the proper drug stock container was retrieved before proceeding with the prescription filling. If an error occurs, the prescription filling will be terminated and an error generated. A predetermined level of user security is required to resolve the error and reset the system operation. The error event will be logged accordingly.

All drug substitutions are recorded in the workflow data depository for later use. Once the fulfillment process has been successfully confirmed, the technician's/pharmacist's 30 user ID bar code is scanned to record the transaction and initiate the printing of a prescription vial label. If the requested drug is dispensed, the label corresponds to the requested drug's attributes, for example, the drug number, drug name, physical properties, pill image, manufacturer/distributor, lot number, and expiration date of the requested drug dispensed to fill the customer's 32 prescription. If a substitution was made, the substitution details are updated when the label is printed such that the label corresponds to the equivalent drug that was actually dispensed. For example, the vial label may include the equivalent drug's attributes, for example, the drug number, drug name, physical properties, pill image, manufacturer/distributor, lot number, and expiration date of the drug dispensed to fill the customer's 32 prescription.

If an error is made during the fulfillment process (e.g., due to an attempt to manually dispense an improper drug, the technician/pharmacist 30 scanned the indicia from a cell in the wrong location, etc.), the fill workstation 16 may be prevented from continuing to operate until cleared by a technician/pharmacist 30 with an appropriate security level. This security check allows immediate notification of errors within the pharmacy and allows the appropriate supervisory personnel to deal with the situation as appropriate. The fill workstation 16 may be cleared by scanning the user ID bar code of the appropriate supervisory user. The date/time that the error event occurred may be logged for the prescription creating the error. Additionally, the drug number of the drug attempted to be dispensed, the filler's user ID, the supervisor's (e.g., pharmacist) user ID, etc. may be logged.

The present invention provides a system and method to solve the problems inherent in other pharmacy systems by managing the allowable medical item substitution based on inventory availability, rules established by regulatory agencies and other interested entities, and others as discussed above, and providing a method for capturing and transmitting the specific prescription data collected for each instance filled by the pharmacy.

In addition to the benefits discussed above, the present invention allows a site to securely manage the medical item substitution rules and list of equivalent medical item products, and directs the technician/pharmacist 30 to use an alternative medical item number and/or retrieve the allowable substitute medical item from an alternative stock location based on various rules.

Additionally, the integrated pharmacy system 10 may alert the technician/pharmacist 30 (visually or audibly) of a pending medical item substitution, alert the technician/pharmacist 30 (visually or audibly) of a change in stock location for a specific medical item, verify that the correct storage container is retrieved from the inventory shelf or stock location (when non-automation equipment is used), verify that the medical item was retrieved from the correct automation device (when automation equipment is used), and accept a technician/pharmacist 30-initiated request to dispense another medical item.

The present invention may prevent the prescription fulfillment process from continuing if an incorrect substitution is attempted, require a supervisory override to clear a substitution error, alert the checking technician/pharmacist 30 that a different medical item substitution was made for a refilled prescription, and alert the technician/pharmacist 30 when a pharmacist or additional override is required due to slight variations in equivalencies. Slight variations in equivalencies may occur, for example, when a brand name product is used instead of generic, generic is used for a brand name product, and the FDA Orange Book equivalencies are not identical (thus, requiring pharmacist and/or physician review and approval). If a slight variation in equivalency is determined, the present invention may allow filling to continue by noting the request to the prescribing doctor, may flag and alert the technician/pharmacist 30 checking the prescription to issue a final okay for dispensing to the customer 32, and may allow a check with future hold at Will Call should doctor approval not be received before the customer 32 arrives.

The present invention may also record a technician/pharmacist 30 identifier with each prescription filled (with or without substitution), record the actual medical item dispensed to an inventory management and re-order system, record the actual medical item quantity dispensed to an inventory management and re-order system, record the actual medical item information to the pharmacy computer system for customer 32 record management, and record prescription filling information in a tracking database for all prescriptions filled (with or without substitutions). Additionally, the present invention may generate and display reports of substitutions by prescription number, and by technician/ pharmacist 30 or personnel, by substitutions (correct, incorrect, with overrides), among others. The present invention may generate records for correct substitutions, incorrect substitutions attempted, and incorrect substitutions with override by technician/pharmacist 30. The present invention may also allow a medical item equivalency list to be imported from an external database or other pharmacy supplied list.

Although the present invention has been described in the context of substitution rules being applied to a requested drug and its equivalents, the application of the substitution rules to a single drug may also provide benefits. For example, if, after adjudication, it is determined that no equivalent drugs are available, the substitution reference list will contain only the requested drug. However, by applying the substitution rules, it may be determined that the requested drug is available in several locations within the pharmacy. Thus, benefits may be obtained by selecting the location having the oldest expiration date, picking the location having the most inventory, picking the location from which the requested drug can be dispensed in the most cost effective manner, etc. Thus, even pharmacies where a substitution reference list cannot be generated or under circumstances where the substitution reference list contains only the requested drug, added value can still be obtained by applying the substitution rules.

It should be recognized that the above-described embodiments of the invention are intended to be illustrative only. A latitude of modification, change, and substitution is intended in the foregoing disclosure, and in some instances, some features of the invention will be employed without a corresponding use of other features.

What is claimed is:

1. A method, comprising:
   receiving prescription information identifying a requested medical item;
   creating a substitution reference list in response to said prescription information, said substitution reference list identifying at least one of said requested medical item or an equivalent medical item;
   automatically applying substitution rules in a database to said substitution reference list to select a medical item from said substitution reference list; and
   automatically outputting dispensing information related to the selected medical item on said substitution reference list.

2. The method of claim 1 wherein said creating a substitution reference list includes determining whether an equivalent medical item may be dispensed in place of said requested medical item.

3. The method of claim 1 wherein said creating a substitution reference list includes comparing said received prescription information to substitution rules provided by one of a prescribing physician, an insurance provider, a government agency, Medicare, Medicaid, a customer, or a pharmacist.

4. A method, comprising:
   receiving prescription information;
   automatically applying substitution rules from a database to said received information; and
   automatically outputting dispensing information related to a medical item selected based on the application of said substitution rules.

5. The method of either claim 1 or claim 4 wherein said substitution rules include rules based on at least one of dispensing system hardware configuration, drug availability, drug expiration date, cost, pharmacy profit potential, inventory management, workflow efficiencies, pharmaceutical considerations, or customer preferences.

6. The method of either claim 1 or claim 4 additionally comprising dispensing in response to said dispensing information.

7. The method of claim 6 wherein said dispensing includes one of automatically dispensing or manually dispensing.

8. The method of claim 6 additionally comprising verifying that said selected medical item has been correctly dispensed.

9. The method of claim 6 additionally comprising generating an alert when an equivalent medical item is dispensed.

10. The method of claim 6 further comprising saving data responsive to said dispensing.

11. The method of claim 6 additionally comprising manually entering a request to dispense an equivalent medical item and generating an alert if said manually entered request is determined to be nonequivalent.

12. The method of claim 6 additionally comprising printing a prescription label based on said dispensing.

13. The method of claim 6 additionally comprising updating an inventory level in response to said dispensing.

14. The method of claim 6 additionally comprising printing medical item attributes in response to said dispensing.

15. The method of either claim 1 or claim 4 additionally comprising generating an alert if a requested medical item or an equivalent medical item are unavailable.

16. A method for manually filling a prescription, comprising:
   receiving prescription information identifying a requested drug;
   automatically applying substitution rules from a database to said received information;
   automatically outputting stock location information based on the application of said substitution rules;
   retrieving a stock bottle based on said stock location information; and
   dispensing from said retrieved stock bottle.

17. The method of claim 16 wherein said substitution rules include rules based on at least one of dispensing system hardware configuration, drug availability, drug expiration date, cost, pharmacy profit potential, inventory management, workflow efficiencies, pharmaceutical considerations, or customer preferences.

18. The method of claim 16 additionally comprising verifying that the correct stock bottle has been retrieved.

19. The method of claim 16 additionally comprising generating an alert when an equivalent drug is dispensed.

20. The method of claim 16 further comprising saving data responsive to said dispensing.

21. The method of claim 16 additionally comprising manually entering a request to dispense an equivalent drug and generating an alert if said manually entered drug is determined to be nonequivalent.

22. The method of claim 16 additionally comprising printing a prescription vial label based on said dispensing.

23. The method of claim 16 additionally comprising updating an inventory level in response to said dispensing.

24. The method of claim 16 additionally comprising printing drug attributes in response to said dispensing.

25. The method of claim 16 additionally comprising generating an alert if said requested drug or an equivalent drug is unavailable.

26. The method of claim 16 additionally comprising creating a substitution reference list based on said received information, and wherein said automatically applying automatically applies said substitution rules to said substitution reference list to select one of said drugs identified on said substitution reference list.

27. The method of claim 26 wherein said creating a substitution reference list includes determining whether an equivalent drug may be dispensed in place of said requested drug.

28. The method of claim 26 wherein said creating a substitution reference list includes comparing said received prescription information to substitution rules provided by one of a prescribing physician, an insurance provider, a government agency, Medicare, Medicaid, a customer or a pharmacist.

29. The method of claim 26 additionally comprising generating an alert if none of the drugs on said substitution reference list are available.

30. A method for automatically filling a prescription, comprising:
receiving prescription information identifying a requested drug;
automatically applying substitution rules from a database to said received information;
automatically outputting information to an automated dispensing device based on the application of said substitution rules; and
automatically dispensing in response to said output information.

31. The method of claim 30 wherein said substitution rules include rules based on at least one of dispensing system hardware configuration, drug availability, drug expiration date, cost, pharmacy profit potential, inventory management, workflow efficiencies, pharmaceutical considerations or customer preferences.

32. The method of claim 30 additionally comprising verifying that a drug has been correctly dispensed.

33. The method of claim 30 additionally comprising generating an alert when an equivalent drug is dispensed.

34. The method of claim 30 further comprising saving data responsive to said dispensing.

35. The method of claim 30 additionally comprising manually entering a request to dispense an equivalent drug and generating an alert if said manually entered drug is determined to be nonequivalent.

36. The method of claim 30 additionally comprising printing a prescription vial label based on said dispensing.

37. The method of claim 30 additionally comprising updating an inventory level in response to said dispensing.

38. The method of claim 30 additionally comprising printing drug attributes in response to said dispensing.

39. The method of claim 30 additionally comprising generating an alert if said requested drug or an equivalent drug is unavailable.

40. The method of claim 30 additionally comprising creating a substitution reference list based on said received information, and wherein said automatically applying automatically applies said substitution rules to said substitution reference list to select one of said drugs identified on said substitution reference list.

41. The method of claim 40 wherein said creating a substitution reference list includes determining whether an equivalent drug may be dispensed in place of said requested drug.

42. The method of claim 41 wherein said creating a substitution reference list includes comparing said received prescription information to substitution rules provided by one of a prescribing physician, an insurance provider, a government agency, Medicare, Medicaid, a customer, or a pharmacist.

43. The method of claim 41 additionally comprising generating an alert if none of the drugs on said substitution reference list is available.

* * * * *